(12) United States Patent
Attard et al.

(10) Patent No.: US 11,942,206 B2
(45) Date of Patent: Mar. 26, 2024

(54) SYSTEMS AND METHODS FOR EVALUATING ENVIRONMENTAL AND ENTERTAINING ELEMENTS OF DIGITAL THERAPEUTIC CONTENT

(71) Applicant: PLAYING FORWARD, INC., Dover, DE (US)

(72) Inventors: John Attard, Franklin, TN (US); Victor Talbot, New York, NY (US); Christopher Recinos, Carson, CA (US); Darren Hocking, Montmorency (AU); Hassan Farhat, Dallas (AU); Harout Mardirosian, Clovis, CA (US); Yudhi Sharma, Los Angeles, CA (US)

( * ) Notice: Subject to any disclaimer, the term of this patent is extended or adjusted under 35 U.S.C. 154(b) by 0 days.

(21) Appl. No.: 18/487,070

(22) Filed: Oct. 14, 2023

(65) Prior Publication Data
US 2024/0038361 A1  Feb. 1, 2024

Related U.S. Application Data

(63) Continuation of application No. 17/706,770, filed on Mar. 29, 2022, now Pat. No. 11,837,349, which is a continuation-in-part of application No. 17/141,039, filed on Jan. 4, 2021, now abandoned.

(60) Provisional application No. 62/959,373, filed on Jan. 10, 2020.

(51) Int. Cl.
| | |
|---|---|
| *G06V 40/20* | (2022.01) |
| *A63B 24/00* | (2006.01) |
| *G06V 10/82* | (2022.01) |
| *G16H 20/30* | (2018.01) |

(52) U.S. Cl.
CPC ......... *G16H 20/30* (2018.01); *A63B 24/0006* (2013.01); *G06V 10/82* (2022.01); *G06V 40/23* (2022.01); *A63B 2024/0009* (2013.01)

(58) Field of Classification Search
CPC ..... A63B 24/0006; G06V 40/23; G06V 10/82
USPC .......................................................... 705/2
See application file for complete search history.

*Primary Examiner* — Kesha Frisby
(74) *Attorney, Agent, or Firm* — Joseph D. Hodler

(57) ABSTRACT

Systems and methods for evaluating the efficacy of entertaining elements during physical and cognitive therapeutic sessions are disclosed. The system is comprised of a means for providing visual and auditory information, and prompting a patient to perform physical and cognitive tasks of varying difficulty. The system is further comprised of a means of tracking the patient's movements to provide feedback to the patient and assess the performance of the patient's movements. Prompted movements are designed to provide therapeutic mental, behavioral, and physical health benefits to the patient, and may increase or decrease in difficulty based on prior assessments of a patient's movements. Entertaining elements are introduced in the visual and auditory information and assessed for their impact on the patient's performance of the movements.

17 Claims, 7 Drawing Sheets

SYSTEMS AND METHODS FOR EVALUATING ENVIRONMENTAL AND ENTERTAINING ELEMENTS OF DIGITAL THERAPEUTIC CONTENT

CROSS-REFERENCE TO RELATED APPLICATIONS

The present application is a continuation of U.S. patent application Ser. No. 17/706,770 filed on Mar. 29, 2022, which claims the benefit of Ser. No. 17/141,039, filed on Jan. 4, 2021, which claims the benefit of Provisional Patent Application No. 62/959,373, filed Jan. 10, 2020.

FIELD

The present disclosure generally relates to digital therapeutics, and more specifically to a comprehensive framework for evaluating environmental and entertaining elements of technology assisted therapeutic systems for enhanced adoption, engagement, and adherence.

BACKGROUND

Consumer available interactive devices, including mobile phones, tablets, smart watches, and virtual reality headsets are becoming more common and provide new opportunities for interacting with users.

Some interactive devices such as virtual reality headsets now include interfaces (e.g., visual displays, speakers, haptic feedback hardware) for presenting content to a user, as well as new sensors (e.g., gyroscopes, accelerometers, cameras, photo detectors, microphones) for measuring physiological activity of a user.

The prevalence of these devices also increases the availability for digital therapeutics. There are occupational therapy, physical therapy, behavioral health, and mental health applications for patients with neurodevelopmental disabilities, who may have limitations in intellectual and adaptive functioning due to difficulties in physical, motor, learning, language, or behavior areas.

However, certain challenges arise with respect to patients adopting the new applications, engaging with the therapy session, and adhering to successive treatments for optimal benefit. Patients may have trouble with adoption, engagement, and adherence because the digital therapeutics are not patient-centered, with respect to the tasks and movements presented as well as the environmental and entertaining elements of the application. Instead, the current digital therapeutics are aimed towards a mass market and focus on the hypothetical average patient.

A new system of digital therapeutics is needed. To increase a patient's performance, the system will learn each patient's preferences for environmental and entertaining elements of the application and learn each patient's individual abilities in physical and cognitive domains. Such an enhanced system will increase adoption, engagement, and adherence to therapeutic processes.

SUMMARY

The invention disclosed is a system for providing digital therapeutics ("DTx") to patients with neurodevelopmental physical and cognitive challenges. The system is comprised of a means for providing visual and auditory stimuli, which prompt physical movements and the performance of various cognitive tasks. The system is further comprised of a means of recording and measuring the movements of the patient, to ascertain the patient's symmetry, skill, and coordination of physical movements, and speed and accuracy of cognitive tasks.

Environmental and entertaining elements of the visual and auditory stimuli are modified according to the preference and performance of each patient to increase adoption, engagement, and adherence. By appealing to the patient's preferences, the system utilizes a unique pathway to enhanced engagement. Environmental elements may include the scenery in the background of the visual display, the characters, and the music.

Physical movements and cognitive tasks are designed to have mental health, behavioral health, and occupational and physical therapeutic benefits. Movement is essential to life, and a patient's increased mobility improves mental health and sense of wellbeing in addition to physical health.

The system will prompt patients to perform various tasks over the course of a session. Prompted movements and tasks are targeted towards multiple domains, and the system may prescribe movements and tasks according to the individual patient's strengths and weaknesses.

The system is generally comprised of interactive user devices, a network connection, a remote server, and software modules.

The user devices provide the means for providing visual, auditory stimuli, and patient input. In one embodiment, the system is comprised of a tablet computer, with a video touchscreen and audio speakers.

A software module provides successive prompts for physical movements and the performance of cognitive tasks. In one embodiment the prompts are delivered through the video and audio outputs by an avatar performing the movements.

The means of recording and measuring the movements of the patient may be a camera and a body tracking software module. One embodiment utilizes the camera in a tablet computer.

Another software module measures the patient's symmetry, skill, and coordination of physical movements, and speed and accuracy of cognitive tasks. Measurements are scored and facilitate the prompting of future physical movements and cognitive tasks of varying difficulty. Scores are associated with one or more physical and cognitive domains. If a particular domain is scored lower than the others, the system may prompt more physical movements or cognitive tasks to strengthen that domain.

The system may provide successive movements and tasks over the course of a session. In one embodiment, a session may take the form of a one-minute dance. In another embodiment, the session may take the form of a three-minute obstacle course. Other time frames and activity themes are envisioned.

When assessing physical movements, the system measures symmetry, skill, and coordination. In one embodiment, the system uses a body tracking module to track seventy-two points on the body. Symmetry is the balancing of the points from left to right, or the patient's general posture. Skill is the speed of executing a movement. Coordination is the measurement of transition between movements.

When assessing cognitive tasks, the system measures skill and accuracy. Cognitive skill is related to speed of initiation and execution of a task. Accuracy is the correctness of a response.

Environmental and entertaining elements are modified between, and throughout, sessions. Environmental elements include visual and audio stimuli. Visual stimuli modifications may generally include color, brightness, and speed of background imagery. Other visual stimuli may be more nuanced and relate to the size and nature of a virtual space or social interactive elements such as eye contact. Audio stimuli modifications may generally relate to volume and tempo, but could relate to pitch, harmony, and tone.

Entertaining elements are modified to determine the effectiveness of familiar characters and themes presented in popular culture on the patient's performance. In one embodiment, an avatar presents example movements to the patient. The avatar may be a popular character from a children's cartoon or movie. For example, the character might be branded intellectual property such as Leonardo from the Teenage Mutant Ninja Turtles, Dora the Explorer, or SpongeBob SquarePants. Other entertaining elements include popular music that appeals to the individual patient.

The system utilizes a software module to calculate a Coefficient of Entertainment ("CoE"). This is a metric designed to demonstrate the effectiveness of modifications to environmental and entertaining elements. As these elements are adjusted, the system measures performance and determines which modifications are causing increases in scores of physical movements and cognitive tasks. In addition to increasing scores and performance, the CoE for each patient also increases the likelihood of adoption of the therapy, engagement during a session, and adherence to a protocol of multiple sessions to address a neurodevelopmental challenge.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not to be considered limiting of its scope, the principles herein are described and explained with additional specificity and detail through the use of the accompanying drawings in which.

DETAILED DESCRIPTION

Figure 1:
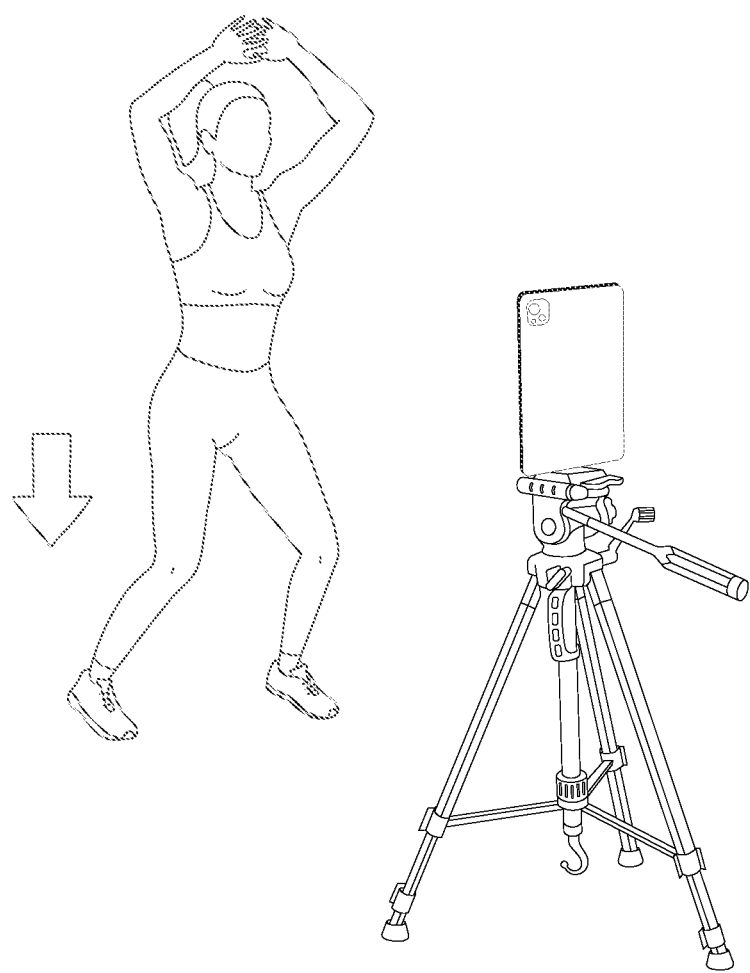
FIG. 1 is a perspective view of a patient performing a jumping jack in front of one embodiment of the invention.

The invention disclosed is a system for providing DTx to patients with neurodevelopmental physical and cognitive challenges, which may affect mental and behavioral health. The system displays prompts for patients to perform physical movements and cognitive tasks with a focus on occupational and physical therapy. The movements are recorded, measured, and scored. Future movements are prescribed based on a patient's performance.

The system adjusts environmental and entertaining elements within the display and accompanying audio. Environmental elements may include the appearance, feel, and setting of the display, and entertaining elements may include well-known characters and music. As patients perform better or worse based on changes to environmental and entertaining elements, the system measures a CoE. Future therapy sessions utilize the CoE to enhance patients' performance, and generally increase adoption, engagement, and adherence.

Coefficient of Entertainment

The present disclosure is directed towards a comprehensive framework for evaluating the intrinsic therapeutic effect of entertaining content. Generally, the CoE encompasses changes to all environmental stimuli, including simple variables such as color, brightness, setting, and pace, in addition to traditional notions of entertainment such as popular characters and music. In the present disclosure the individual terms "environmental" and "entertaining", with respect to interactive elements, may refer to environmental and entertaining elements collectively, and are generally called Entertaining Elements.

The CoE is constantly adjusting based on feedback in a closed loop system. An initial dataset corresponding to Entertaining Elements is scored against a patient's performance. As Entertaining Elements are adjusted, and the patient's performance improves or declines, a CoE is calculated for the changes in elements for each individual patient. The CoE is then used to inform the dataset for subsequent therapy sessions.

Closed Loop System

Several datasets are embodied in the closed loop system. These datasets may generally be grouped: Entertaining Elements, Prescribed Movements, Difficulty of Movements, Performance of Movements. Throughout this disclosure, movements include physical movements but may also include cognitive tasks, as the cognitive tasks are embedded in a physical movement. A patient may perform a cognitive task by interacting with virtual objects. For example, the patient may perform a math problem by moving virtual objects into groups or may perform a memory exercise by turning over virtual cards.

An initial dataset of Entertaining Elements encompasses the audio and video displays. During a session, the system prompts a set of Prescribed Movements. Each movement has a level of difficulty, maintained in a Difficulty of Movements dataset. The patient performs each movement according to their ability during that session, and the system records a dataset corresponding to the Performance of Movements. The performance is scored based on the difficulty of the movements, and the system finds correlations between the patient's performance and the Entertaining Elements.

This correlation is the CoE, which may be used in continuing sessions with the individual patient to enhance performance on a subsequent session. The CoE is constantly updating based on changing Entertaining Elements and patient performance. The CoE is a measurement to train the system on how to find patterns linking Entertaining Elements to patient performance and is also a tool to develop future Prescribed Movements to challenge the patient and improve the effectiveness of therapeutic sessions.

System Components

In one embodiment, the system is comprised of three general categories of components: patient devices, network connections, and remote server. In alternative embodiments, a patient device may encompass an entire system. However, the best mode envisions a network connection to a remote server providing software backend processing and regular updates of Entertaining Elements and Prescribed Movements.

One embodiment of the invention utilizes consumer-accessible technology for patient devices. Generally, a patient device is comprised of a means for displaying Entertaining Elements, prompting Prescribed Movements, recording patient movements, and receiving patient input.

One embodiment of the invention utilizes a computer tablet with a touchscreen, audio speakers, and camera. The touchscreen provides a means for display and patient input. The speakers provide audio for Entertaining Elements and prompting movements. The camera records the patient's movements for measurement and analysis. The computer tablet may be positioned at a distance from the patient to view the patient's entire body performing movements during a session. Alternatively, a smartphone with a front facing camera is also possible. FIG. 1 shows an image of a patient performing a movement in front of a computer tablet mounted on a tripod. The computer tablet provides visual and audio output, a network connection and means for patient input.

An alternative embodiment of the invention utilizes a virtual reality headset and a separate camera for recording the patient's movements. The headset provides video and audio output to the patient and is connected to controllers for receiving patient input. The separate camera is positioned at a distance to record the patient's full body. Currently available virtual reality headsets include the HTC Vive, Oculus Rift, Oculus Quest, and Pico Neo 2.

Figure 2:
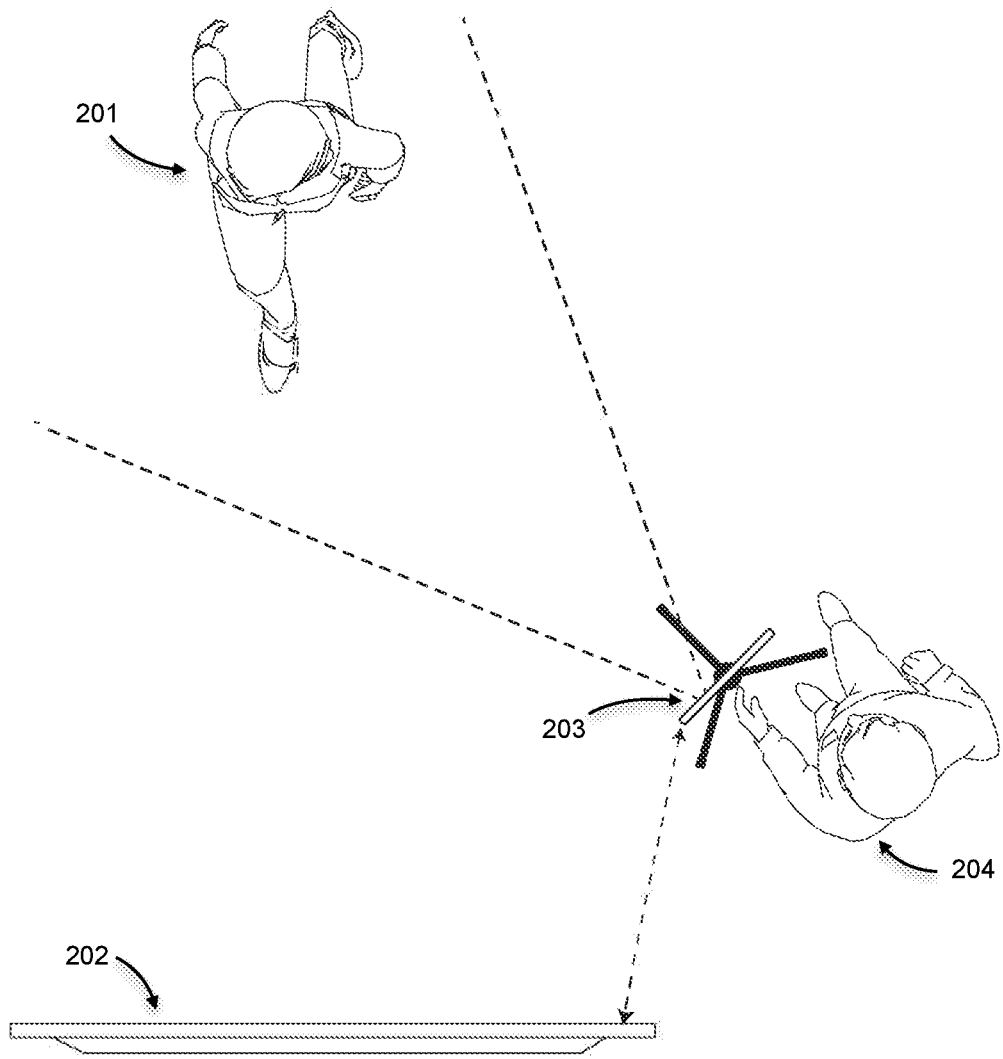
FIG. 2 is an overhead view of a patient performing a movement in front of one embodiment of the invention, with an observer.

Alternative embodiments of the invention may include separate components for the display of visual elements, transmission of audio, input from the patient, and recording the patient's movements. Visual displays may be through any type of digital screen, a computer monitor, television screen, a video projector, or lighting display. Audio may be a separate speaker system. Patient input may be through a separate smartphone, personal computer, or other user interface. FIG. 2 shows an overhead view of a patient 201 performing a movement in front of an embodiment of the invention with a large visual display 202 and separate camera 203.

The means of recording the patient's movements may be a separate camera. An example camera may be a Microsoft Kinect V2 with motion capture technology, and Long Short-Term Memory facilitation through a recurrent neural network. Another example may be an Azure Kinect with convolutional neural networks. Two-dimensional cameras from smartphones and webcams may apply, as well as three-dimensional cameras including those found on Apple iPhones and iPads with MocapX motion capture technology.

Additional devices may be incorporated for recording and measuring patient physiological data. Such devices may include accelerometers for measuring movements, sensors for detecting heart rates, or cameras for tracking eye movements.

Figure 3:
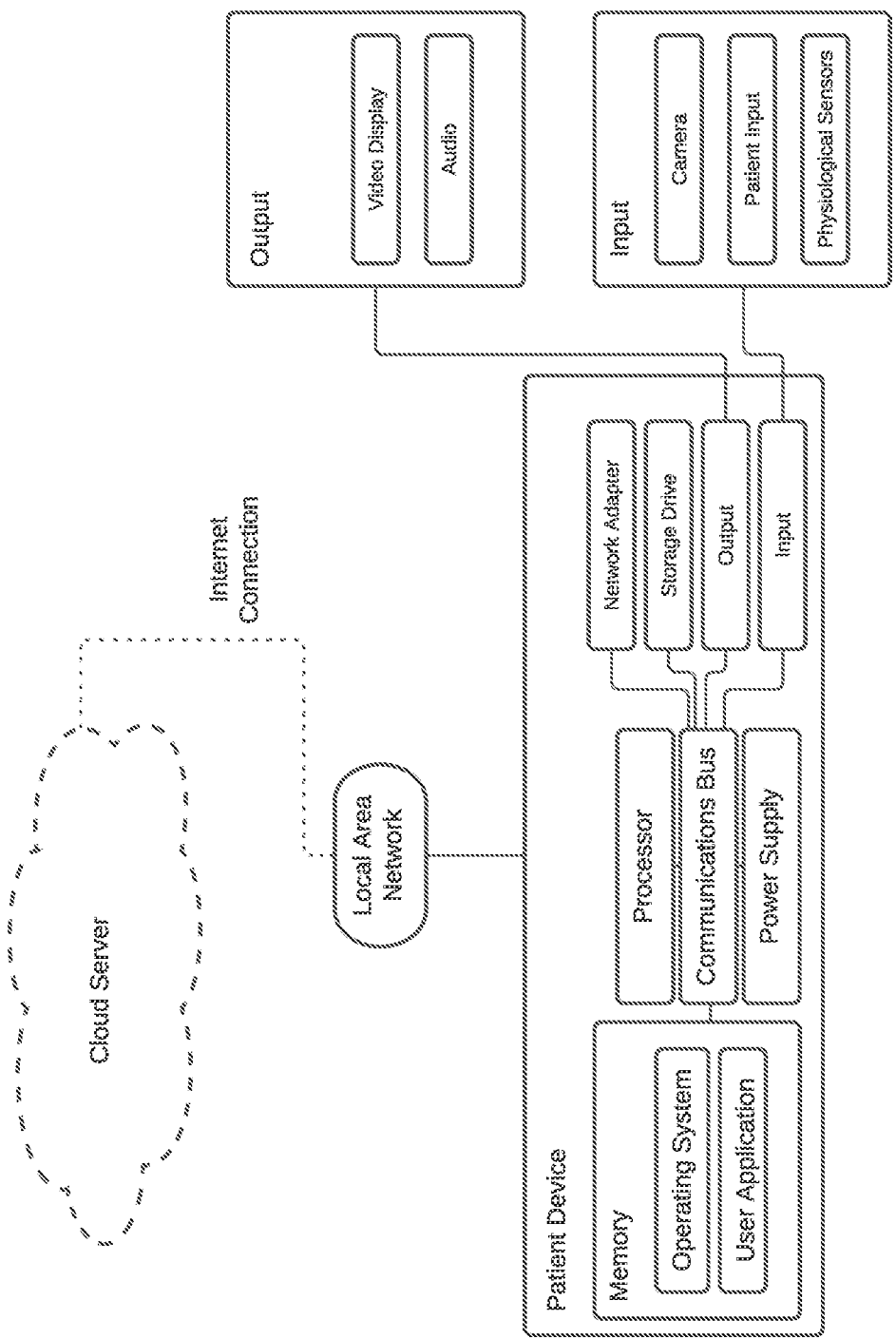
FIG. 3 is a system diagram of one embodiment of the invention, showing a patient device.

FIG. 3 shows a system diagram of a patient device's components. The device is comprised of at least one network interface, at least one processor, a memory connected to a communications bus, input and output interfaces, and a power supply.

The memory is comprised of a plurality of storage locations that are addressable by the processor for storing software programs and data structures associated with the examples described herein. In general, the memory hosts the operating system and a user application for running the method.

The processor may comprise necessary elements or logic adapted to execute the software programs and manipulate data structures. The processor can include one or more programmable processors (e.g., microprocessors or microcontrollers, or fixed-logic processors). In the case of a programmable processor, any associated memory, may be any type of tangible processor readable memory (e.g., random access, read-only), that is encoded with or stores instructions that can implement program modules (e.g., a module having process encoded thereon). The processor can also include a fixed-logic processing device, such as an application specific integrated circuit ("ASIC") or a digital signal processor that is configured with firmware comprised of instructions or logic that can cause the processor to perform the functions described herein. Thus, program modules may be encoded in one or more tangible computer readable storage media for execution, such as with fixed logic or programmable logic (e.g., software/computer instructions executed by a processor), and any processor may be a programmable processor, programmable digital logic (e.g., field programmable gate array), or an ASIC that comprises fixed digital logic, or a combination thereof. In general, any process logic may be embodied in a processor or computer readable medium that is encoded with instructions for execution by the processor that, when executed by the processor, are operable to cause the processor to perform the functions described herein.

Illustratively, the user application process and/or process may be performed by hardware, software, and/or firmware, which may contain computer executable instructions executed by the processor to perform functions relating to evaluating the intrinsic therapeutic effect of content presented to a patient and optimizing content based on the same, as described herein.

It will be apparent to those skilled in the art of computer engineering that other processor and memory types, including various computer-readable media, may be used to store and execute program instructions pertaining to the techniques described herein. Also, while the description illustrates various processes, it is expressly contemplated that various processes may be embodied as modules configured to operate in accordance with the techniques herein (e.g., according to the functionality of a similar process). Further, while the processes have been shown separately, those skilled in the art will appreciate that processes may be routines or modules within other processes.

In one embodiment, the patient device also has input and output interfaces. An output interface may link to a video screen for displaying images generated by the user application. An additional output interface may link to audio speakers for projecting sound associated with prompted movements and associated music or other Entertaining Elements.

In one embodiment, the input interfaces connect to a means of capturing the patient's movements and other input. Input means may include a camera for recording video of a patient's body, a touchscreen or computer peripherals for entering information to control the user application, and physical sensors for recording movements or physiological data from the patient.

Network

In one embodiment, the patient device is connected to the Internet through a local area network. See FIG. 4. The network interface contains the mechanical, electrical, and signaling circuitry for communicating data over links (e.g., wires or wireless links) within a network. The network interface may be configured to transmit and/or receive data using a variety of different communication protocols, as will be understood by those skilled in the art.

A communication network is a geographically distributed collection of nodes interconnected by communication links and segments for transporting data between end nodes, such as mobile devices, computers, personal computing devices, and other devices. Many types of networks are available, ranging from local area networks ("LANs") to wide area networks ("WANs"). LANs typically connect these nodes over dedicated private communications links located in the same general physical location, such as a building or campus. WANs, on the other hand, typically connect geographically dispersed nodes over long-distance communications links, such as common carrier telephone lines, optical light paths, synchronous optical networks ("SONET"), synchronous digital hierarchy ("SDH") links.

As shown, the patient device communicates and exchanges data (e.g., traffic and/or messages) with a remote server using predefined network communication protocols such as certain known wired protocols (e.g., Interior Gateway Protocol ("IGP"), Exterior Border Gateway Protocol ("E-BGP"), TCP/IP), wireless protocols (e.g., IEEE Std. 802.15.4, WiFi, Bluetooth®), PLC protocols, or other shared-media protocols where appropriate. In this context, a protocol consists of a set of rules defining how the nodes interact with each other. The particular data exchanged between the patient device and the remote server can include, for example, movement prompts and environmental elements for shaping the content of a session, as well as the measured data corresponding to movements and input from the patient.

Remote Server

Alternatively, it is also appreciated that one or more components of a patient device may be incorporated into a larger distributed computing environment. For example, in a distributed computing environment, the individual components of the patient device may represent logical or virtual components, where such components are implemented and hosted by a data center (e.g., using servers, distributed memory, communication links/networks, software modules, services, objects, distributed data structures).

Those skilled in the art of computer engineering will understand that any number of nodes, devices, communication links, and the like may be used, and that the view shown herein is for simplicity. Those skilled in the art will also appreciate that the particular components of the system are illustrated for purposes of example and discussion, and further the processes for evaluating the intrinsic therapeutic effect of content presented to a user, determining the therapeutic CoE metric for such content, and optimizing the content based on the same may be configured for implementation by various types of systems.

Figure 4:
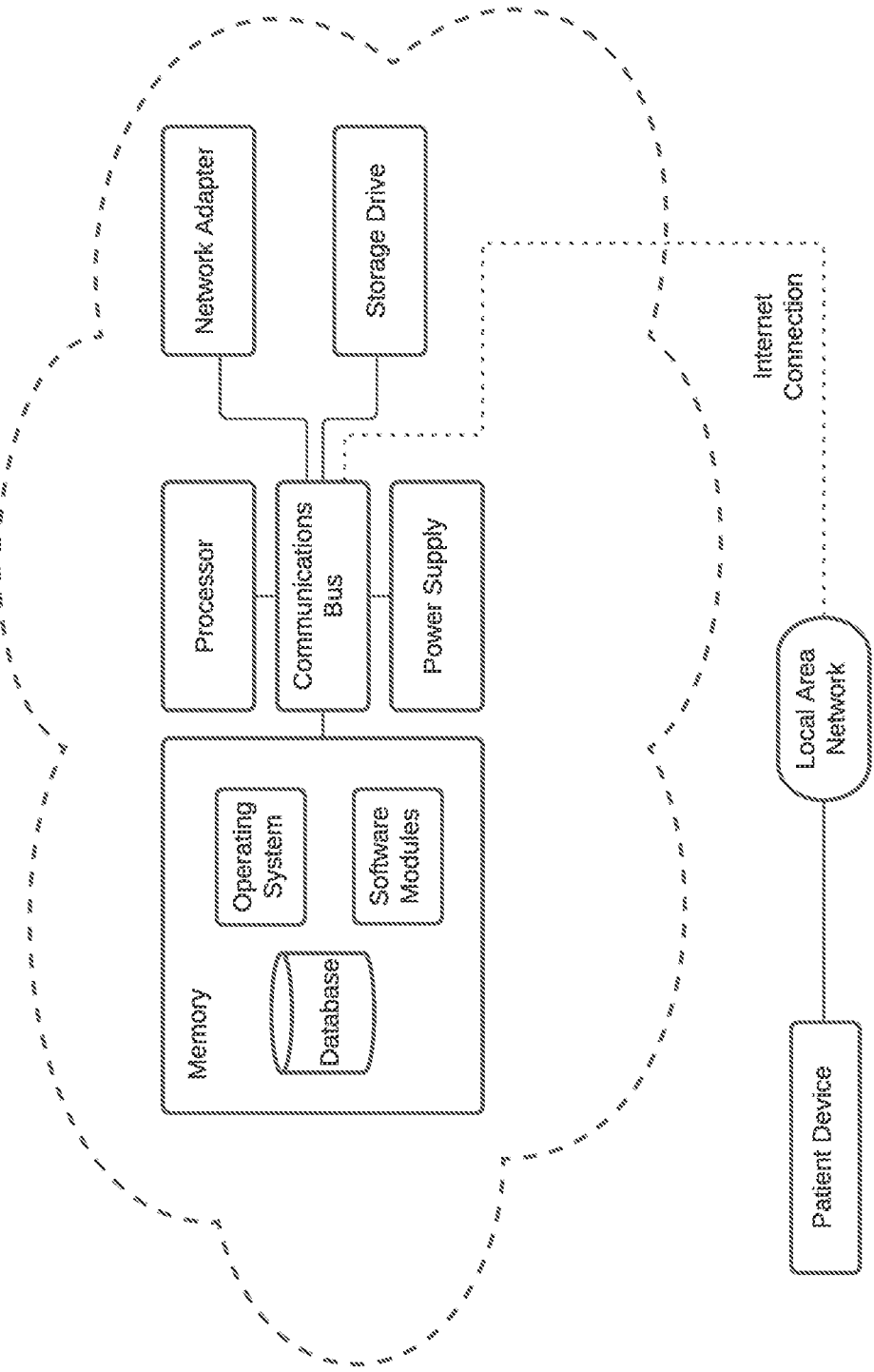
FIG. 4 is a system diagram of one embodiment of the invention showing a remote server.

FIG. 4 shows one embodiment of the contents of a remote server. The remote server operates as a virtual machine for hosting data and processing logic, receiving patient data, and transmitting prompts for movements, cognitive tasks, and environmental elements of a session. In one embodiment the remote server is comprised of a virtual machine with a memory, processor, communications bus, and power supply. The memory is comprised of an operating system, software modules for processing, and a database of multiple datasets.

Figure 5:
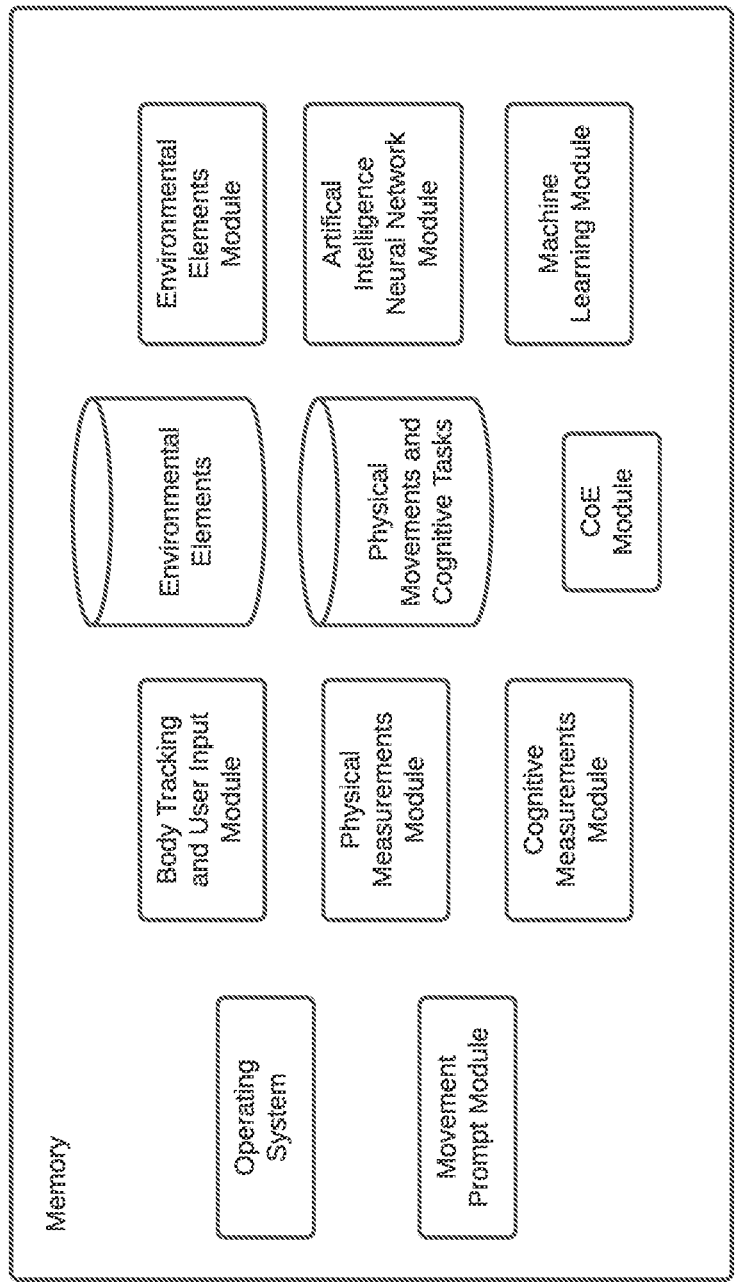
FIG. 5 is a diagram of one embodiment of the invention, showing data and software modules in the memory of a remote server.

FIG. 5 shows one embodiment of the memory hosted on the remote server. Memory components include an operating system for managing databases and software modules. An operating system, portions of which are typically resident in memory and executed by a processor, functionally organizes the virtual machine by, inter alia, invoking operations in support of services and/or software processes executing on the device.

In one embodiment, one database is comprised of Environmental Elements and another database is comprised of Physical Movements and Cognitive Tasks. Example datasets may include Entertaining Elements, Prescribed Movements, Difficulty of Movements, and Performance of Movements.

Entertaining Elements refer to environmental elements including visual and audio stimuli. In a literal sense, the entertaining element may be an element known from popular culture, such as cartoon character or song familiar to the patient. Other entertaining elements may include the look and feel of the visual and audio output. Example visual elements may include color, brightness, and speed of background imagery. Audio elements may include volume, tempo, pitch, harmony, and tone. An Entertaining Elements dataset records the application and degree of the various elements in each session.

Some embodiments of the invention utilize gameplay characteristics. These may be considered Entertaining Elements and include reward mechanisms to encourage successful performance of the various tasks. Rewards may include audio and visual effects, a point system, and encouragement from other characters within the game.

Prescribed Movements refer to the physical movements provided by the Movement Prompt Module. Movements may include jumping jacks, half jumping jacks, standing on one leg, a side jump, a forward jump, skip, lunge, hop, jog in place, touch the nose, touch the knee, etc. The Prescribed Movements dataset records the application of the movements in each session.

Difficulty of Movements refers to the difficulty of a movement in a particular domain, and the overall difficulty of the movement across all domains. Movement domains may include balance, bi-coordination, gross motor skills, and motor planning Each movement has a weight for each movement domain, with a cumulative difficulty score.

Performance of Movements refers to the symmetry, skill, and coordination of physical movements, and the cognitive skill and accuracy of movements associated with cognitive tasks. The Performance of Movements dataset records the degree of symmetry, skill, coordination, cognitive skill, and accuracy of the patient as measured by the Body Tracking and user Input Module.

Software System

As shown in FIG. 5, in one embodiment, the memory is further comprised of an Operating System and multiple software modules. The Operating System coordinates inputs from the patient's device through the various modules, informed by the datasets, to provide visual and audio output to the patient in the form of movement prompts.

Figure 6:
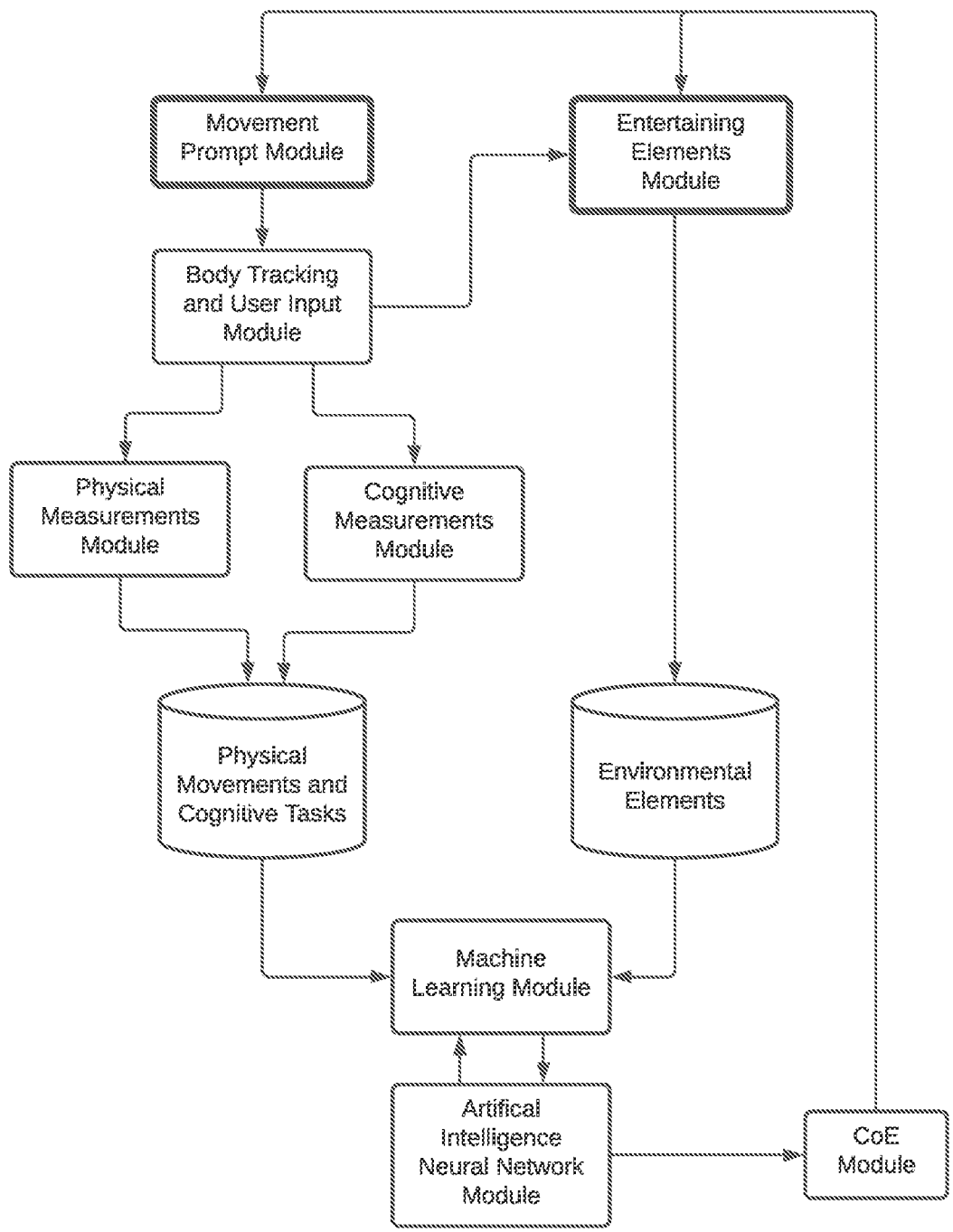
FIG. 6 is a flow chart showing the calculation of a CoE and how it is used to inform changes to prompted movements and adjustments to environmental and entertaining elements.

FIG. 6 demonstrates the flow of data through the various modules to create evolving Prescribed Movement prompts based on patient performance. The prompts are developed through a closed loop, with each successive movement, or session, informed by the performance of previous movements, or sessions.

The process begins with a Movement Prompt Module prompting a movement from the Prescribed Movements dataset, which is then displayed to the patient through the visual and/or audio output. A Body Tracking and User Input Module may record patient preferences for Entertaining Elements and feed them to an Entertaining Elements Module.

The Body Tracking and User Input Module also records the patient's movements and relays the information to a Physical Measurements Module to assess the symmetry, skill, and coordination of the movement. In parallel, the movement may also be relayed to a Cognitive Measurements Module in the case of physical movements associated with cognitive tasks. These movements are also measured for cognitive skill and accuracy. Data is stored in the Performance of Movements dataset and supplied to a Machine Learning Module.

The Machine Learning Module finds patterns in the data. Particularly, the module is assessing correlations between Entertaining Elements and Performance of Movements. Continual use of the system and input of patient performance aids the Machine Learning Module in training a model to identify more precise and continually evolving patterns.

The Machine Learning Module informs an Artificial Intelligence Neural Network Module to develop weights for determining future Prescribed Movements and Entertaining Elements. These future Prescribed Movements and Entertaining Elements are embodied in the CoE, designed to facilitate, and optimize, patient engagement and performance during a therapeutic session. The CoE is stored in a CoE Multidimensional Array, consisting of weights for all movements and elements.

The CoE Module then transfers the adjusted CoE back to the Movement Prompt Module and the Entertaining Elements Module for adjustments to future Prescribed Movements and Entertaining Elements. As the Movement Prompt Module displays the next movement, the process continues, to further determine the appropriate CoE for each patient at each moment in each session.

Artificial Intelligence

An Artificial Intelligence Neural Network Module provides dynamic prompts for movements. One embodiment of the invention utilizes a Recurrent Neural Network ("RNN"), which provides real-time feedback to update input variables. In one embodiment, the RNN is modeled in TensorFlow Lite, and written using C #. The prompted movements may focus on areas of weak performance. The goal of this module is to increase the overall score of a session, by increasing the difficulty of Prescribed Movements in various domains. Increasing the overall scores is an indication of an increase a patient's neuromotor development in the focused domains.

The Artificial Intelligence Neural Network Module may be called an AI model, which predicts a patient's performance improvements when applying the CoE to Entertaining Elements and Prescribed Movements. In one embodiment, the AI model is a hybrid of Bayesian inference and a deep neural network, utilizing both stochastics and heuristics.

The Bayesian component is the stochastic, random side. Bayesian components do not use fixed weights but incorporate probability distributions to provide uncertainty estimates for predictions. The AI model includes aleatoric uncertainty, inherent in natural variability, and epistemic uncertainty, inherent in the system.

The AI model also includes heuristics to prescribe the best movements. Heuristics are useful in AI to search for a dataset that closely correlates to observations. Heuristics also speed up the AI search algorithm.

In one embodiment, the AI model utilizes an adaptive staircase algorithm to ensure optimal engagement. In seeking increased engagement, the model adjusts stimuli and difficulty levels to target a 75% to 85% performance measurement. It is believed that this level is rewarding enough to the patient to keep them engaged but challenging enough to provide therapeutic value. As a patient's performance increases, stimuli and difficulty may increase to maintain the 75% to 85% target. Alternatively, stimuli and difficulty may decrease to account for a lower performance level.

The staircase operates by increasing or decreasing parameters of elements or difficulty of Prescribed Movements by a threshold estimate. These changes, reflected in the CoE, are designed to test a parameter's range, and determine optimal Prescribed Movements and Entertaining Elements.

Other heuristics are programmed into the AI model to aid engagement. These rules enforce variance in Prescribed Movements, Entertaining Elements, and other parameters defining a session. Heuristics may apply as parameters to the Movement Prompt Module or to patient input. An example may be a limit on the number of times a patient may select a particular session targeting a group of movements, or a limit on the successive times a patient may select a background or accompanying audio. For example, a particular session may be limited to ten times in a row, or a movement may be limited to fifteen repetitions in any one session.

In one embodiment, the AI model utilizes deep learning, with multiple layers of neural networks between inputs from the Body Tracking and User Input Module and the model outputs formulated in the CoE. The AI model can look at high and low-level patterns to get a richer analysis of inputs to outputs.

In one embodiment, the AI model utilizes Long Short-Term Memory for deep learning. The AI model is a recurrent neural network, with feedback connections between the model outputs (the CoE) and the model inputs (Prescribed Movements, Difficulty of Movements, Entertaining Elements, and Performance of Movements). The model needs to identify patterns across multidimensional datasets, all input parameters, and develop a multidimensional CoE for predicting and driving increased performance.

In some embodiments, the AI model may also include social intelligence for recognizing and simulating emotions and mood, which may further enhance performance and engagement.

Machine Learning

AI models must be trained to identify data correlations and predict future output. The invention utilizes inputs from the Body Tracking and User Input Module in addition to Entertaining Elements and Prescribed Movements. The invention uses a means of capturing volumetric motion of the body. One embodiment of the invention uses a camera to monitor the patient, with motion tracking software to find landmarks points on the body. Example points include the crown of the head, base of the neck, sternum, center of the abdomen, center of the pelvis, outer point of the deltoids, elbows, wrists, hips, knees, ankles, etc. The tracking of more landmark points enhances the invention's ability to measure and improve motor skills.

The invention may utilize commercial body tracking systems, such as Google PoseNet or Apple ARKit. These, and other body tracking solutions, provide robust tracking of patients in various conditions. It is preferable that the body tracking can handle changes in lighting, distance from the patient, different camera types, and multiple body shapes and sizes.

As the patient performs movements, the body tracking system uses object recognition to follow landmark points, joint coordinates, on the body and perceive the patient's movements in relation to the prompted movement.

In one embodiment, the body tracking follows a data transformation pipeline to identify the pose of the body. The joint coordinates are transposed in space relative to the position of the body in the camera. They are transposed to the center of the screen based on the patient's right hip.

After transposition, the joint coordinates are normalized relative to the patient's height. One embodiment does this by measuring the distance between a shoulder and elbow of a patient's arm. All distances are scaled, using this measurement, to a normalized height in the AI model. After transposition and normalization, the joint coordinates are rotated such that the body is facing the camera.

This joint coordinate data transformation is done several times per second. Positioning, normalizing, and rotating the joint coordinates reduces variance when recognizing motion.

In one embodiment, the system gathers data from seventy-two joint coordinates on the patient's body. If the joint coordinates follow an existing pattern for a pose or movement between poses, the data is determined valid. The pose or movement is then compared to optimal point positions for that patient. The difference is scored as a performance measurement of the movement.

Machine learning strategies may be categorized as classification or pattern recognition. Classification is used to gather a multidimensional dataset and determine the significance of the data by scoring it. Classification may be used by the invention to determine the significance of Entertaining Elements, such as the introduction of a popular character. Pattern recognition is used to determine whether a dataset meets a predefined class. Pattern recognition may be used by the invention to determine whether a patient's movement meets expectations. For example, pattern recognition may determine whether a patient is properly performing a jumping jack by determining whether their hands fully touch above the head and their feet jump apart horizontally.

In one embodiment, a hybrid supervised model trains the AI model. Unsupervised learning is used to gather initial training data, comparing the processed output to the target output. As the model learns, it becomes more supervised. Alternative embodiments of the invention may utilize supervised, unsupervised, or semi-supervised machine learning models.

In addition to body tracking, some embodiments collect real-time data across multiple modalities. These may include eye movements, skin conductance, heart rate, EEG, or other biometrics.

Prescriptive Movements

The invention prescribes movements to the patient to provide occupational and physical therapeutic benefits, with the goal of promoting the advancement of various physical and cognitive domains. During a session, Prescribed Movements may highlight a patient's strengths as well as focus on the development of a patient's weaknesses. Each movement is scored in the Performance of Movements dataset and weighted by the Difficulty of Movements dataset. Future Prescribed Movements are designed to challenge the patient and improve the effectiveness of therapeutic sessions, based on their past performance and difficulty of the movements.

Physical Movements

Prescribed Movements focus on occupational and physical therapy movements for enhancing motor skills. Example movements include jumping jacks, half jumping jacks, standing on one leg, a side jump, a forward jump, skip, lunge, hop, jog in place, touch the nose, and touch the knee. Multiple movement domains, such as gross motor skills, balance, motor planning, and coordination are incorporated.

A variety of motor skills testing systems are available. One embodiment of the invention uses the Bruininks-Oseretsky Test of Motor Proficiency, Second Edition Short Form ("BOT-2").

Body Domains

In addition to movement domains, the invention also focuses on body domains. These include individual parts of the body, such as a finger, hand, foot, or head. Domains may also be the grouping of parts into a larger domain, such as the upper arm, entire leg, upper body, lower body, whole body, whole spine, or head and neck. One embodiment of the invention utilizes seventy-two different physical points, each representing a domain, and grouped to form larger body domains.

Physical Movement Measurements

The system records the movements. The changes in movement of the landmark points are measured, and provide data for analysis of symmetry, coordination, and speed. The system evaluates performance of movements and may provide the patient with feedback. One embodiment provides feedback in the form of a score.

The Performance of Movements dataset stores the measurements for each movement preformed. Each movement is measured and scored in isolation, but they are also measured in temporal relation. A session is a series of Prescribed Movements, and a patient is required to transition from one movement to the next. These transitions may be more or less difficult depending on the difference between the successive movements. For example, transitioning between a jumping jack and a ski lunge is arguably harder than transitioning between a one-legged balance and a yoga tree pose. The former transition requires a higher degree of coordination and balance to execute. At the end of each session, an assessment is made examining the weakest domain during that session. A new session targeting the weaker domain may be prescribed.

Measuring the improvement of motor skills is evident in the increased scores of symmetry, coordination, and speed of performing a movement in subsequent sessions. The increase in these categories may translate into improvement of other health factors, including ACE-2 activation and cardiovascular health.

Cognitive Tasks

The invention also tests cognitive skills through a variety of tasks. Cognitive skills may also be divided into several domains. Example cognitive domains include inhibitory control, attention switching ability, working memory, visual-spatial ability, and mathematics. Other cognitive domains are also envisioned.

Inhibitory control is the ability to stop a thought process to focus on something new. Inhibitory control is useful to adapt to environments with changing stimuli, where a previous action is no longer appropriate.

Attention switching is essentially the ability to multi-task. The patient is required to perform one task and then required to switch to another task. The patient may be prompted to switch back to the first task, required to switch back and forth between two tasks several times, or between three or more tasks.

Attention switching and inhibitory control may work in tandem. When one task is prompted over another, the patient must practice inhibitory control over the first task to concentrate on the second task. Attention switching is measured as a cost of the diminished speed and accuracy of the second task.

Working memory, also called short-term memory, is the ability to hold information temporarily and apply it appropriately. It is useful for decision-making and behavior.

Visual-spatial ability is mentally manipulation of a two-dimensional or three-dimensional object.

Cognitive tasks may be embodied in Prescribed Movements. Example movements may include stacking objects by number or touching virtual reality objects to solve a memory problem. The difficulty of the cognitive tasks is embodied in the Difficulty of Movements dataset.

A variety of cognitive tasks may be presented to the patient during a session. One embodiment of the invention has the patient interacting in a virtual reality environment. The patient is given a simple mathematical test and is asked to signal the answer through a movement, such as touching the correct answer. Another version of an additional task might be placing virtual objects in a container until a designated number is reached.

Another embodiment might include an attention switching challenge involving two separate tasks. The first task might be an association memory game, and another task might be a simple math problem. The patient may be given a word and a color to memorize, then given a math problem to solve, and then prompted to recall the word using the color as a prompt. Attention switching tasks work multiple cognitive skills at once. This example requires the patient to use working memory to remember the word and color, to use inhibitory control to stop focus on the memory task, to switch focus to a math problem, and then to use math skills to solve the math problem. Then, the patient must use memory recall to present the word.

Several types of cognitive tasks are available, including the following:

An N-back task is a task where a patient must remember whether a stimulus matched a previous stimulus from N steps ago. This means a patient needs to keep N number of stimuli in working memory. An example might include a spatial position of an object in a field. The object is moved one time, and then a second time. The patient is given a blank field and asked to recreate the first position. This is a 2-back task. If the patient were asked to recreate the second position, this would be a 1-back task. Generally, the larger the N, the harder the task.

A Spatial Span task is the presentation of an arrangement of objects, that change over the course of multiple iterations. A patient is then required to recreate the sequence of arrangements. An example Spatial Span task might be a three-by-three grid of nine squares. One square is shaded in the first iteration, a second square is shaded in a second iteration, and so on. The patient is then asked to repeat the sequence of shaded squares.

A Visually Array Change Detection task measures visual working memory. An array of objects in a field are presented. Some of the objects are modified, and the array is displayed again. The patient is asked to determine how many, or in what way the objects were modified.

An alternative Change Detection task may also be presented with a distraction element, to measure the working memory.

A Stop Signal task is the differentiation between two stimuli given at random. Two different responses are required for the different stimuli. Response time and accuracy are recorded.

A Go/No-go task tests inhibitory control. Two stimuli are given, with one prompting a positive action, such as pressing a button, and the second prompting a negative action, such as refraining from pressing the button. Response time and accuracy are recorded.

A Modified Stroop test measures selective attention, cognitive flexibility, and processing speed. A typical Stroop test presents two incongruent stimuli, such as a word for a color written in a different color. The word "yellow" might be written in blue color. The patient is asked to identify the color of the word, and not the word itself. Response time and accuracy are measured.

A Flanker test measures inhibitory control. Three types of stimuli are provided, congruent, incongruent, and neutral. Stimuli are given at random, and the patient is asked to provide appropriate responses.

Additional tests include those provided in the National Institute of Health's NIH Toolbox. This includes over one hundred stand-alone measurements for cognition, emotion, motor skills and sensations.

Cognitive Task Measurements

Cognitive tasks may be measured by skill (speed of initiation and execution of a task) and accuracy (correctness of a response). Some tasks are objectively more difficult than others and receive greater weight. Over the course of a session, a patient may engage in multiple tasks of various difficulty.

The difficulty of cognitive tasks, and of the collective tasks of an entire session, are dynamically balanced such that a patient experiences a minimum level of success in completing the tasks. If the patient is experiencing errors or slow response times, easier tasks may be presented. If the patient is experiencing a high rate of success, more difficult tasks may be presented.

Joint Physical Movement and Cognitive Task Measurements

Cognitive domains and physical domains are tested simultaneously. The difficulty levels of the cognitive tasks and the physical tasks are coordinated such that one or both are increased or decreased to modify the overall level of difficulty. On the other hand, the difficulty of the cognitive and physical tasks may move inversely, to ease one domain in order to enhance the ability to solve a harder task in the other domain. Cognitive and physical measurements are maintained to assess the correlation between domains, as well as the causation of one domain in enhancing the abilities of the other.

Entertaining Elements

Prescribed Movements provide the therapeutic value of the invention, but the Entertaining Elements are what drive the patient. The CoE is more than just an aesthetic, enhancing the patient's experience. It also improves the patient's performance during a session. This is measured by monitoring the patient's cognitive and physical performance with respect to adjusting the Entertaining Elements in the CoE.

Entertaining Element parameters may be grouped into four categories. These include visual, auditory, familiarity, and pacing. Entertaining Element parameters may be discrete or continuous.

Visual parameters include lighting, style, color pallet, background setting, and the perceived size of the virtual space. Each parameter, and its degree of implementation, is stored in the Entertaining Elements dataset. For example, the brightness of colors, or the flashing of lights are measured as inputs to the Machine Learning Module and are correlated with performance to adjust the CoE.

Some embodiments of the invention are equipped with a means for producing audio. Auditory parameters include volume and pitch, as applied to speech, music, and sound effects. A specific use of volume could be the adjustment of decibel strength in coordination with proximity, to signify a far-off subtle sound from a close-up whisper. Other parameters may include the total number of auditory queues, or the number of background noises.

Familiarity refers to the personal preference of, or familiarity to, an Entertaining Element. One example might be a particular song, musical artist, or genre of music. One embodiment of the invention utilizes music familiar in popular culture. Another example might be a particular character, such as a cartoon or superhero. One embodiment of the invention incorporates branded intellectual property to provide the patient with their favorite character. A further example of familiarity is the repeated use of parameters selected by the patient or otherwise implemented by the AI model. As the patient increases adherence, more data is available with respect to which elements are familiar.

Pacing refers to the overall feel of the session. Pacing includes a variety of aspects, that create a sense of timing with respect to movements. Example environmental parameters that relate to pacing include, the tempo or rhythm of the audio, the proximity and direction of spatial effects, the emotion of the content, aspects of animation (reserved, lively, emotive tone, aggressive or passive interactivity with the patient), background movement, dialogue, and visual special effects.

CoE Calculation

The CoE is a multidimensional array comprised of all the variable parameters of the system. It is a measurement of the therapeutic value of Entertaining Elements as they apply to Performance of Movements (various physical and cognitive tasks). Variable parameters of the system include the physical movements, cognitive tasks, environmental and entertaining elements, and other session parameters.

Parameters associated with physical movements include a value for each movement as well as the affected domains of each movement. Movement domains may include balance, coordination, gross motor competency, and motor planning Various movements require a higher level of skill across the movement domains. For example, a jumping jack requires a higher level of coordination than standing in a yoga tree pose, but the yoga tree pose requires a higher level of balance than the jumping jack. Each movement carries a value for each of the domains.

Parameters associated with cognitive tasks include a value for each task as well as the affected cognitive domains. These domains may include attention switching, inhibitory control, working memory, visual-spatial ability, and mathematics. Each cognitive task has a value related to its relative difficulty in the cognitive domain.

Parameters associated with Entertaining Elements are also included in the CoE. Some parameters are discrete and will carry a 1 if used, or a 0 if not used. Other parameters are continuous and will carry a value from 0 to 1 depending on the degree of use. A potential continuous variable might be the volume of sound effects or the pace of the background scenery. an example discrete variable might be use of branded character as an avatar or the use of a particular song. Entertaining Elements may have multiple parameters associated with a single element. Other session parameters might include the length of a session, and gameplay features such as rewards.

For ease of explanation, each parameter is normalized on a scale of 0 to 1. For continuous parameters, the value may be any decimal between 0 and 1. For discrete parameters, the value may be 0 for not used or 1 for used. All values across all parameters total to 100. If there are more than 100 variables, the values are normalized to a lower decimal and represented from 0 to a decimal x.

As movements are prompted and performed by the patient, the system will score each movement from 0 to 1. A score of 0 is poor and a score of 1 is perfect. The patient will probably score somewhere between 0 and 1. The values of parameters will change over time.

If a patient is performing a task or movement relating to a certain parameter well, the value of that parameter will decrease. If a patient is scoring low in a certain parameter, the value of that parameter will increase. These decreases and increases in parameters are recorded in the changing CoE, and will affect future changes to Entertaining Element parameters as well as the Prescribed Movements.

The degree and rate of change of parameters are also parameters. Modest changes to parameters may be desirable for some patients, whereas others may show more rapid progress and ability to master new movements and tasks. In one embodiment, the CoE is calculated 60 times per second, and alterations to Prescribed Movements and Entertaining Elements may be made at that rate. However, such immediate feedback could create instability in the model. In one embodiment, changes to the CoE are implemented in real time during a session. In an alternative embodiment, changes to the CoE are only reflected in subsequent sessions.

Figure 7:
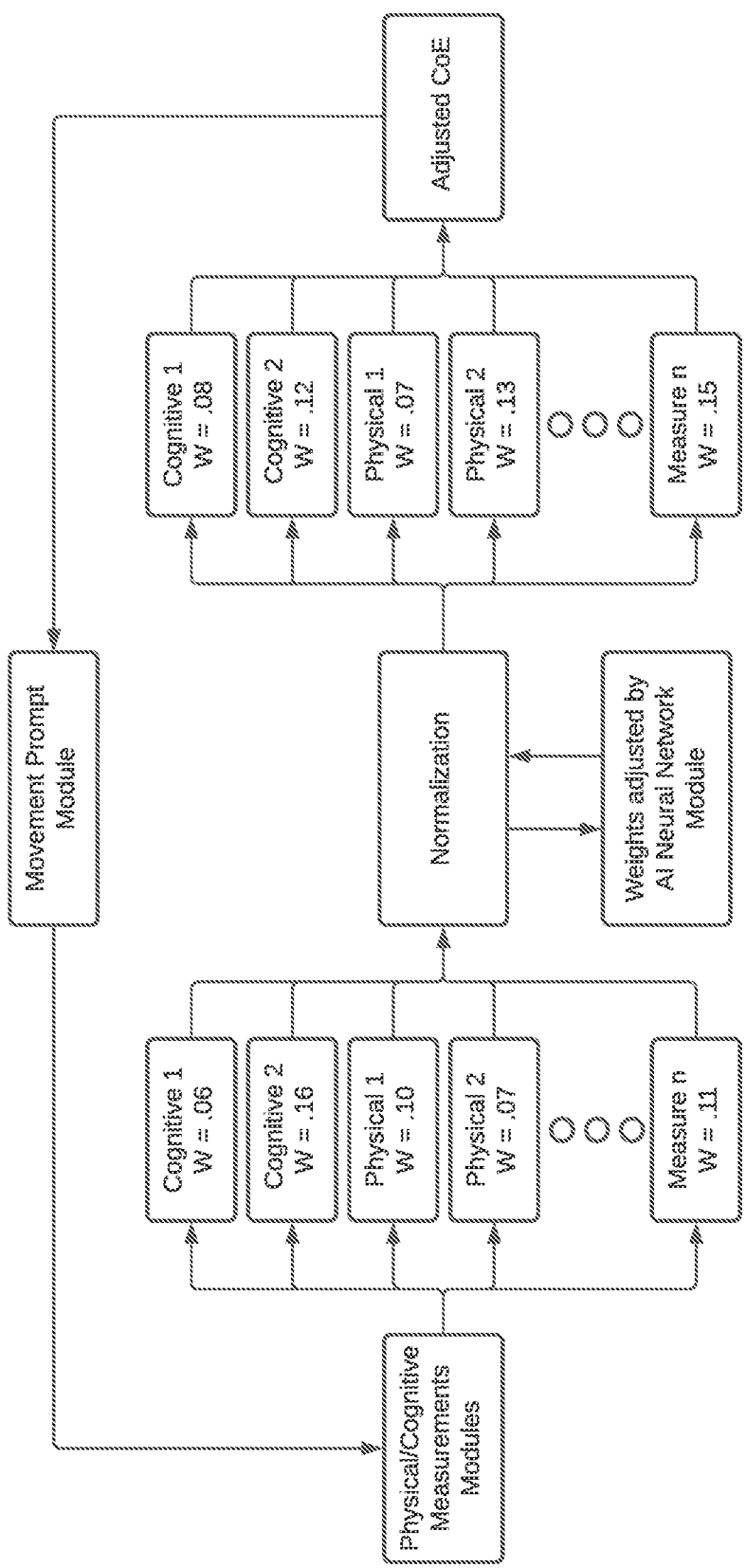
FIG. 7 is a flow chart showing adjustments to weighting factors of multiple parameters.

FIG. 7 shows a high-level CoE flow diagram of how cognitive and physical parameters are adjusted. Entertaining Elements and other session parameters follow the same process. Cognitive parameters include cognitive tasks and cognitive domains affected by those tasks. Physical parameters include physical movements and movement domains. The weight of each parameter is measured based on the patient's performance, and then adjusted up or down by the Artificial Intelligence Neural Network Module into an adjusted CoE. The new CoE informs the Movement Prompt Module regarding new physical movements and cognitive tasks.

User Input

In one embodiment, the patient or another party may provide input to the Body Tracking and User Input Module for incorporation into a therapeutic session. A user may input the selection of particular movements or the length of the session. A user may also select Entertaining Elements to incorporate into the audio and visual displays.

For example, a patient may determine which branded intellectual property characters to incorporate, or which music to play during the session. Allowing the selection of preferences may empower the patient to direct an aspect of their therapy and further increase engagement.

Feedback

The invention includes real-time feedback, and delayed processing feedback. Real-time feedback provides the patient with an avatar performing the same movements through motion tracking. Feedback may also come in the form of encouragement from the avatar and gamification in the form of points or rewards for successful movements.

Delayed processing feedback provides an overall analysis of the session, including the patient's cognitive and physical performance.

Observer Assessments

Some embodiments further utilize a human observer 204. See FIG. 2. Envisioned observers include parents, teachers, caretakers, researchers, and therapists, in person or remotely. The invention is an inexpensive method of improving mental health, behavioral health, and performing occupational and physical therapy in a variety of scenarios. The invention works under many lighting conditions, spatial constraints, camera types, and body shapes.

One potential use could be the assessment of patients with autism spectrum disorder. An observer may supplement the invention by also assessing autistic traits during a session with the Social Responsiveness Scale developed by John Constantino.

Another potential use could be assessment of patients with Attention Deficit Hyperactivity Disorder. An observer may supplement the invention by also assessing ADHD traits during a session with the Conners Scale developed by C. Keith Conners.

Another role for an observer might be the measurement of everyday executive functions using the Behavior Rating Inventory of Executive Function-2 ("BRIEF-2").

CONCLUSION

While there have been shown and described illustrative examples of the comprehensive framework for determining a CoE for DTx-based content and for optimizing the presentation of content based on the same, it is to be understood that various other adaptations and modifications may be made within the spirit and scope of the embodiments herein. Thus, while the foregoing description has been directed to specific embodiments, it will be apparent that other variations and modifications may be made to the described embodiments, with the attainment of some or all their advantages. Accordingly, this description is to be taken only by way of example and not to otherwise limit the scope of the embodiments herein.

What is claimed is:

1. A method for providing a series of customized therapeutic movements and entertaining elements to a patient, performed on a computer system with at least a memory, processor, and a power supply, the method comprising:
   a) transmitting visual information to a patient's device with a user interface, prompting the patient to perform movements,
   b) transmitting entertaining elements to the patient's device in the form of visual information, while the patient performs the prompted movements, where the entertaining elements include an avatar and a background setting,
   c) receiving information from the patient's device regarding the patient's posture throughout the movements,
   d) assessing the patient's performance of the movements, with a software module in the memory,
   e) continuously finding correlations between the patient's performance and the parameters associated with the entertaining elements, and
   f) in accordance with the correlations, continuously adjusting parameters associated with the entertaining elements in real-time to affect the patient's performance of subsequently prompted movement.

2. The method of claim 1, wherein the computer system may be in the patient's device or in a remote server.

3. The method of claim 1, further comprised of transmitting entertaining elements to the patient's device in the form of audio information.

4. The method of claim 3, wherein the audio information is music.

5. The method of claim 4, wherein the adjusting of parameters pertains to the rhythm of the music.

6. The method of claim 3, wherein the audio information is speech.

7. The method of claim 1, wherein the adjusting of parameters pertains to the familiarity of an entertaining element.

8. The method of claim 1, wherein the adjusting of parameters pertains to the pacing of an entertaining element.

9. The method of claim 1, wherein the adjusting of parameters pertains to the mood of an entertaining element.

10. The method of claim 1, wherein an artificial intelligence neural network recommends movements based on the assessment of the patient's performance.

11. The method of claim 1, wherein a prompted movement is associated with a cognitive task.

12. The method of claim 11, where in the prompted movements are designed to improve a patient's management of cognitive control.

13. The method of claim 1, wherein the entertaining elements are animated.

14. The method of claim 1, wherein the adjusting of parameters is designed to improve the patient's adherence to the therapy.

15. The method of claim 1, wherein the prompted movements are designed to improve a patient's physiological management.

16. The method of claim 1, where in the prompted movements are designed to improve a patient's management of movement skills.

17. The method of claim 1, wherein the prompted movements are designed to improve a patient's mental health.

* * * * *